United States Patent [19]

Takata

[11] 4,036,704
[45] July 19, 1977

[54] LIQUID CHROMATOGRAPHICAL METHOD

[75] Inventor: Yoshinori Takata, Ibaraki, Japan
[73] Assignee: Hitachi, Ltd., Japan
[21] Appl. No.: 419,353
[22] Filed: Nov. 27, 1973
[30] Foreign Application Priority Data
  Dec. 11, 1972  Japan ........................ 47-123344
[51] Int. Cl.² ............... B01D 15/08; G01N 27/42
[52] U.S. Cl. ........................... 204/1 T; 23/230 R;
       73/61.1 C; 204/195 R
[58] Field of Search ............ 204/1 T, 195 R;
       210/31 C; 73/61.1 C; 23/230 R, 253 R; 324/29

[56] References Cited
U.S. PATENT DOCUMENTS

| | | | |
|---|---|---|---|
| 3,461,042 | 8/1969 | Martin et al. | 204/1 T |
| 3,580,832 | 5/1971 | Rhodes | 204/195 T |
| 3,582,475 | 6/1971 | Pretorius et al. | 204/1 T |
| 3,594,294 | 7/1971 | Pretorius et al. | 204/195 R X |
| 3,649,498 | 3/1972 | Pretorius et al. | 204/195 R X |
| 3,759,816 | 9/1973 | Pretorius et al. | 204/195 R X |

*Primary Examiner*—G. L. Kaplan
*Attorney, Agent, or Firm*—Craig & Antonelli

[57] ABSTRACT

A separation column for separating and developing a sample to be analyzed is connected to a pump for feeding an eluting solution at an end of the separation column. A means for introducing the sample to be analyzed is provided between the pump and the separation column. Another end of the separation column is connected to an electrochemical detection means through a mixing means. To the mixing means is connected a pump for feeding a catalyst solution capable of promoting an electrode reaction of the sample contained in an eluate solution. A mixture solution of the eluate solution and the catalyst solution from the mixing means is fed to a detection means to quantitatively determine the sample.

5 Claims, 3 Drawing Figures

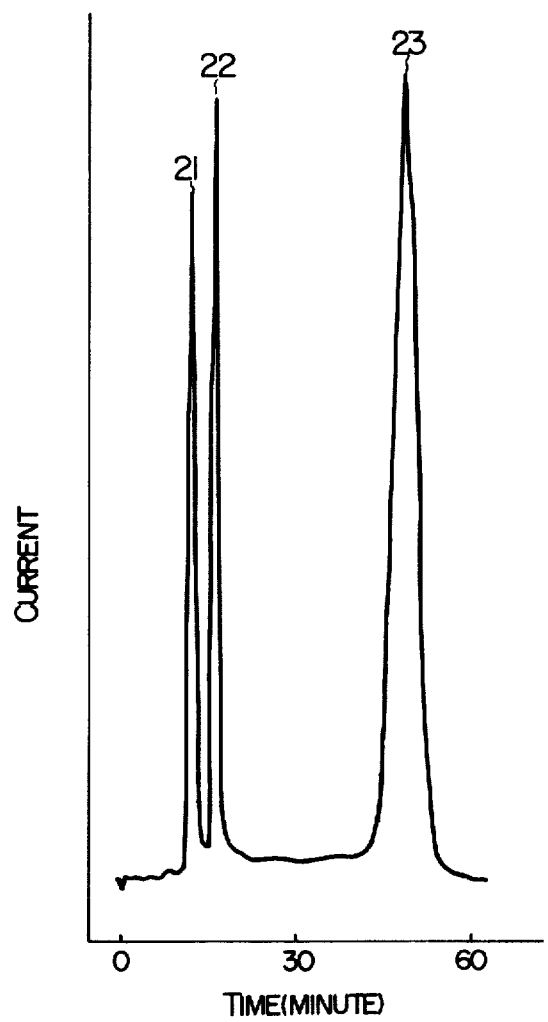

LIQUID CHROMATOGRAPHICAL METHOD

BACKGROUND OF THE INVENTION

This invention relates to a method and apparatus for carrying out liquid chromatography, and more particularly to a method and apparatus for carrying out liquid chromatography which can effectively detect samples having a difficult electrolytic oxidation when an eluate solution from a separation column is electrochemically detected.

Liquid chromatography can be applied to analysis of a wide range of materials through a combination of various columns and detectors. However, an appropriate detector has not been available for detecting some kind of materials, for example, sulfur compounds, etc., and it is difficult to detect very small amounts of these materials.

Among the liquid chromatographic methods of detection, for example, an ultra-violet absorptiometric method generally has a high sensitivity, but is selective, and thus can be utilized only for the detection of materials having absorptions in an ultra-violet range. The ultra-violet absorptiometric method is not suitable for measurement of sulfur compounds. Other methods of detection, for example, a refractometric method or thermo-detective method, have a universal applicability, but a low sensitivity of detection. Furthermore, a radioactivity-detecting method has a high sensitivity, but cannot be universally applied owing to its restriction to handling.

Electrochemical detection methods, for example, polarography or coulometry, generally have a sensitivity as high as that of the ultra-violet absortiometric method, but are selective, and thus have no universal applicability. However, the methods can detect some of sulfur compounds such as $H_2S$, etc., though their sensitivity of detection is low, and thus are expected to have a possiblity to detect a very small amount of sulfur compounds.

In the conventional liquid chromatography provided with the electrochemical detector, it is impossible to detect sulfur compounds, for example, $S^{2-}$, $HS^-$, $SO_3^{2-}$, $HSO_3^{2-}$, $S_2O_3^{2-}$, $S_2O_3^{2-}$, $S_4O_6^{2-}$, etc. with a high sensitivity, because these sulfur compounds have a large overvoltage and their electrolytic oxidation is thus difficult to carry out.

SUMMARY OF THE INVENTION

An object of the present invention is to provide a method and apparatus for carrying out liquid chromatography, which can detect samples having a high overvoltage with a high sensitivity by electrochemical detection.

Another object of the present invention is to provide a method and apparatus of analysis for detecting sulfur compounds with a high sensitivity.

These objects can be attained in the present invention in the following manner: in a liquid chromatography by separating and developing samples to be analyzed in a separation column and detecting the samples by electrochemical detection, a catalyst is added to the samples to be analyzed to promote electrode reaction; samples having a high overvoltage are oxidized or reduced on the electrode by catalytic action, and electric currents based on the electrode reaction are detected.

BRIEF DESCRIPTION OF THE DRAWINGS

FIG. 3 is a diagram showing a result of analysis of sulfur compounds by liquid chromatography of the present invention.

DETAILED DESCRIPTION OF THE PREFERRED EMBODIMENT

Sulfur compounds have a low oxidation-reduction potential, and thus are sufficiently electrically active. Therefore, if there is a catalyst to lower an overvoltage, the sulfur compounds separated in the separation column can be detected with a high sensitivity by electrochemical detection. It is seen from the principle of the present invention that an applicability of the present invention is not limited only to the analysis of sulfur compounds, but also to the analysis of materials whose determination has been so far difficult in the conventional liquid chromatography owing to the high overvoltage.

It has been confirmed by experiments that one or a mixture of $I^-$, $MnO_4^-$, $Mn^{2+}$, $Co^{2+}$, $Pb^{2+}$, $Fe^{2+}$, $Fe^{3+}$, $Cu^{2+}$, $SnC_4$, mannitol, glycerin, methanol, etc. are effective as materials capable of promoting electrode reaction of sulfur compounds. A dilute acidic solution of 0.1 N to several N is preferable as the catalyst solution for detecting the sulfur compounds, and a neutral or alkaline solution is not appropriate, because it fails to suitably reduce the overvoltage.

Now, the present invention will be explained by way of one embodiment.

Figure 1:
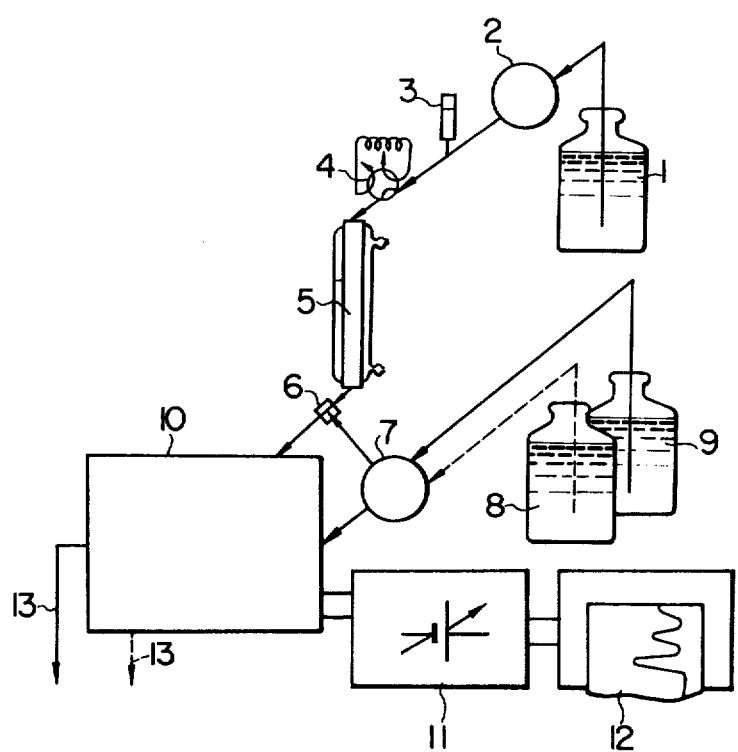
FIG. 1 is a flow sheet of units showing one embodiment of the present invention.

In FIG. 1, an embodiment of apparatus for analyzing sulfur compounds is illustrated, where numeral 1 is an eluting solution, which can proceed with separation and development of samples to be analyzed, 2 a pump for feeding the eluting solution, and 3 a damper for preventing pulsation of the eluting solution. Numeral 4 is a sampler for introducing a sample to be analyzed into a passage for the eluting solution, and the sampler is provided with a six-way switch valve. The sample to be analyzed can be charged into the sampler 4 in advance. Numeral 5 is a column packed with anion exchange resions for separating and developing the samples. Numeral 9 is a catalyst solution containing $Cu^{2+}$, which can promote electrode reaction of the sample contained in the eluate solution from the column 5, and is supplied from a feed pump 7. Numeral 8 is an electrolytic solution to be fed to a compartment oposite to the electrode of coulometrical detection cell 10. The eluting solution 1, the electrolytic solution 8 and the catalyst solution 9 are stored in the respective containers. Numeral 6 is a mixer for mixing the eluting solution from the column 5 with the catalyst solution 9 and feeding the resulting mixture solution to the detection cell 10. The pump 7 is of duplex type, which means that the pump consists of a pair of separate pump units, and can feed the electrolytic solution 8 and the catalyst solution 9 at the same time. The mixture solution from the mixer 6 is electrochemically detected by the coulometrical detection cell 10 consisting of pass-through type electrolytic cell, a detection cell power source 11 for giving a definite potential to the detection cell 10, and a recorder 12 for recording the electric current.

In the liquid chromatography based on such a construction, the eluting solution 1 is fed to the column 5 by the pump 2 through the damper 3 and the sampler 4. The sample charged in the sampler 4 in advance is conveyed to the column 5 by the eluting solution 1 through switching of the valve of the sampler 4. The sample containing sulfur compounds are separated into the respective components by differences in affinities towards the anion exchange resin when the sample passes through the column 5, and the respective components are successively eluted from the bottom of the column 5. The eluate solution from the column 5 is mixed in the mixer 6 with the $Cu^{2+}$ solution 9 continuously fed by the duplex pump 7, and fed to the detection cell 10.

The detection cell 10 has two compartments partitioned by a diaphragm therein, and a working electrode is provided in one compartment, and an auxiliary electrode in another compartment. The solution from the mixer 6 passes through the compartment containing the working electrode, and the electrolytic solution 8 passes through the compartment containing the auxiliary electrode. A definite potential, for example, 0.8 volts, is applied to the working electrode vs auxiliary electrode. In the cell 10, the sulfur compounds to be analyzed are oxidized by electrolysis. The electrolytic solution 8 is fed to the compartment opposite to the electrode of the detection cell 10, but is thrown away as a waste solution 13 after the electrolysis. Likewise, the sample solution oxidized by electrolysis in the detection cell 10 is thrown away as a waste solution 13. The electric current obtained in the detection cell 10 is recorded in the recorder 12. The catalyst solution 9 used in this example is a hydrochloric acid solution containing $Cu^{2+}$, and the electrolytic solution 8 fed to the compartment opposite to the electrode of the detection cell is a mixture solution of potassium ferricyanide and potassium ferrocyanide.

Table 1 shows comparison of effects of addition of various catalytic materials upon the electrolytic oxidation of sulfur compounds, where the detection sensitivities of added catalyst solutions are compared with the detection sensitivity only of a 0.46 N hydrochloric acid solution as a basis. The detection sensitivities towards $SO_3^{2-}$, $S^{2-}$ and $S_2O_3^{2-}$ are made higher by the addition of the catalyst solutions than only by the hydrochloric acid solution. Even only by the addition of the hydrochloric acid solution, the detection sensitivity is considerably improved over that obtained by the conventional liquid chromatography based on the electrochemical detection procedure, but especially effect of $Cu^{2+}$ is distinguished among other catalysts. The effect of the catalyst addition is also observable upon polythionic acids such as $S_2O_6^{2-}$, $S_3O_6^{2-}$, etc. in addition to said sulfur compounds.

Table 1

| Component to be detected | Catalyst and its concentration (M) | | Comparison of detection sensitivities |
|---|---|---|---|
| $SO_3^{2-}$ | | 0.46 N HCl only | 1.00 |
| | $I^-$ | $2.3 \times 10^{-5}$ | 1.75 |
| | $Mn^{2+}$ | $2.3 \times 10^{-5}$ | 1.60 |
| | $Co^{2+}$ | $2.3 \times 10^{-5}$ | 1.52 |
| | $Pb^{2+}$ | $2.3 \times 10^{-5}$ | 1.58 |
| | $Cu^{2+}$ | $1 \times 10^{-5}$ | 1.92 |
| | $Cu^{2+}$ | $2.3 \times 10^{-5}$ | 1.89 |
| | $Cu^{2+}$ | $2.3 \times 10^{-6}$ | 1.92 |
| | $Cu^{2+}$ | $2.3 \times 10^{-7}$ | 1.10 |
| $S^{2-}$ | | 0.46 N HCl only | 1.00 |
| | $I^-$ | $2.3 \times 10^{-5}$ | 1.17 |
| | $Mn^{2+}$ | $2.3 \times 10^{-5}$ | 1.88 |

Table 1-continued

| Component to be detected | Catalyst and its concentration (M) | | Comparison of detection sensitivities |
|---|---|---|---|
| | $Co^{2+}$ | $2.3 \times 10^{-5}$ | 1.50 |
| | $Pb^{2+}$ | $2.3 \times 10^{-5}$ | 2.54 |
| | $Cu^{2+}$ | $1 \times 10^{-5}$ | 4.17 |
| | $Cu^{2+}$ | $2.3 \times 10^{-5}$ | 3.29 |
| | $Cu^{2+}$ | $2.3 \times 10^{-6}$ | 2.96 |
| | $Cu^{2+}$ | $2.3 \times 10^{-7}$ | 2.50 |
| $S_2O_3^{2-}$ | | 0.46 N HCl only | 1.00 |
| | $I^-$ | $2.3 \times 10^{-5}$ | 1.12 |
| | $Mn^{2+}$ | $2.3 \times 10^{-5}$ | 0.97 |
| | $Co^{2+}$ | $2.3 \times 10^{-5}$ | 0.93 |
| | $Pb^{2+}$ | $2.3 \times 10^{-5}$ | 0.80 |
| | $Cu^{2+}$ | $1 \times 10^{-5}$ | 1.21 |
| | $Cu^{2+}$ | $2.3 \times 10^{-5}$ | 1.13 |
| | $Cu^{2+}$ | $2.3 \times 10^{-6}$ | 1.18 |
| | $Cu^{2+}$ | $2.3 \times 10^{-7}$ | 1.05 |

Figure 2:
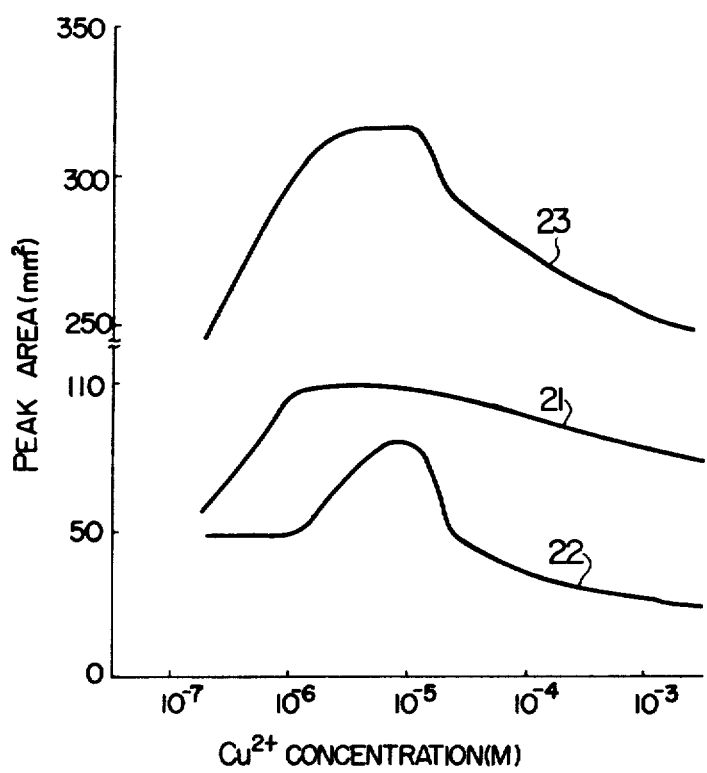
FIG. 2 is a diagram showing relations between the concentration of cupric ions and the effect of catalyst addition.

The detection sensitivity depends also upon the concentration of the catalyst solution in addition to the kind of the catalyst in the present invention. FIG. 2 shows a relation between the $Cu^{2+}$ concentration and the catalytic effect. In FIG. 2, 21 stands for $SO_3^{2-}$, 22 $S^{2-}$, and 23 $S_2O_3^{2-}$. These sulfur compounds exhibit maximum sensitivity when the $Cu^{2+}$ catalyst solution is added to the sample solution so that the $Cu^{2+}$ concentration takes $1 \times 10^{-5}$ M, and also can be detected with a high sensitivity between the concentrations of from $10^{-6}$ to $10^{-4}$ M.

FIG. 3 shows results of analysis by liquid chromatography through the addition of catalyst, where 21 stands for $SO_3^{2-}$, 22 $S^{2-}$, and 23 $S_2O_3^{2-}$. These three sulfur components are contained equally in quantity of $10^{-6}$ moles, and the catalyst solution is a 2 N hydrochloric acid solution containing $10^{-4}$ M $Cu^{2+}$, and is added to the column eluate solution. According to the conventional procedure, $S^{2-}$, that is, 22, can be detected only to a small degree, but $SO_3^{2-}$, that is, 21, and $S_2O_3^{2-}$, that is, 23, cannot be detected. Thus, the sulfur compounds, whose analysis with a high sensitivity has been regarded as difficult in the conventional liquid chromatography, can be completely separated, and analyzed with a high sensitivity in the present invention.

In the foregoing liquid chromatography, the coulometrical detector is used, but another means utilizing the same electrode reaction, for example, a detection means by polarography, utilizing an inactive electrode such as platinum electrode, etc. as an indicator electrode, that is, all of the electrochemical detection means based on the measurement of electric currents by electrode reaction, can be utilized in the present invention in principle. Furthermore, the conventional liquid chromatography provided with the electrochemical detector can be modified to have a function to analyze various samples by providing a means for feeding the catalyst solution to the liquid chromatography in a freely detachable manner as described above, the substances, a very small amount of which has been so far regarded as difficult to detect in the conventional liquid chromatography, for example, sulfur compounds, can be analyzed with ease and high sensitivity in the present invention, and thus the range of application of the liquid chromatography is widely expanded by employing the present invention. Thus, the practical effect of the present invention is considerably high.

What is claimed is:

1. A process for measuring the quantity of at least one electrolytically oxidizable component selected from the group consisting of $S^{2-}$, $HS^-$, $SO_3^{2-}$, $HSO_3^{2-}$, $S_2O_3^{2-}$, $S_2O_6^{2-}$, $S_3O_6^{2-}$, and $S_4O_6^{2-}$ and contained in an eluate solution obtained from a liquid chromatographic separation column, said process comprising mixing with said eluate solution a catalyst, comprising $Cu^{2+}$ in a dilute acid solution effecting catalytic oxidation of said at least one electrolytically oxidizable component, and measuring the electric current produced by said catalytic oxidation.

2. The process of claim 1, wherein the concentration of catalyst in said eluate solution is about $10^{-6}$ to $10^{-4}$ M.

3. The process of claim 2, wherein the concentration of catalyst in said eluate solution is about $10^{-5}$ M.

4. A process for measuring the quantity of at least one electrolytically oxidizable component selected from the group consisting of $S^{2-}$, $HS^-$, $SO_3^{2-}$, $HSO_3^{2-}$, $S_2O_3^{2-}$, $S_2O_6^{2-}$, $S_3O_6^{2-}$, and $S_4O_6^{2-}$ and contained in an eluate solution obtained from a liquid chromatographic separation column, said process comprising mixing with said eluate solution a catalyst selected from the group consisting of $I^-$, $MnO_4^-$, $Mn^{2+}$, $Co^{2+}$, $Pb^{2+}$, $Fe^{2+}$, $Fe^{3+}$, $Cu^{2+}$, $SnCl$, mannitol, glycerin and methanol, effecting catalytic oxidation of said at least one electrolytically oxidizable component by contacting the mixture of the eluate solution and the catalyst with a working electrode and supplying an electrolyte to an auxiliary electrode separated from said working electrode by a diaphragm, said auxiliary electrode and said working electrode being maintained at a constant voltage difference, and measuring the electric current produced by said catalytic oxidation.

5. The process of claim 4, wherein said electrolyte is a solution of potassium ferricyanide and potassium ferrocyanide.

* * * * *